(12) United States Patent
Dewey et al.

(10) Patent No.: US 7,009,692 B2
(45) Date of Patent: Mar. 7, 2006

(54) ARRANGEMENT FOR MONITORING THE POWER DELIVERY OF A PHOTON CHANNELING ELEMENT

(75) Inventors: David A. Dewey, Sunnyvale, CA (US); Nubar S. Manoukian, Cupertino, CA (US); Edward D. Reed, Sunnyvale, CA (US)

(73) Assignee: Lumenis Inc., Santa Clara, CA (US)

( * ) Notice: Subject to any disclaimer, the term of this patent is extended or adjusted under 35 U.S.C. 154(b) by 0 days.

(21) Appl. No.: 10/322,773

(22) Filed: Dec. 19, 2002

(65) Prior Publication Data

US 2003/0174309 A1      Sep. 18, 2003

Related U.S. Application Data

(63) Continuation-in-part of application No. 09/602,442, filed on Jun. 23, 2000, now abandoned.

(60) Provisional application No. 60/147,562, filed on Aug. 6, 1999.

(51) Int. Cl.
*G01N 21/00* (2006.01)

(52) U.S. Cl. .................................... 356/73.1
(58) Field of Classification Search ............. 356/73.1, 356/215–218, 273; 372/43–50, 96, 99, 92, 372/31, 33; 250/211; 369/116; 385/48–49, 385/88; 438/460, 239; 156/250; 437/209
See application file for complete search history.

(56) References Cited

U.S. PATENT DOCUMENTS

| | | | |
|---|---|---|---|
| 4,385,832 A | 5/1983 | Doi et al. | |
| 4,556,875 A | 12/1985 | Ishiwatari | |
| 4,580,557 A | 4/1986 | Hertzmann | |
| 4,812,641 A * | 3/1989 | Ortiz Jr. ................ 250/205 |
| 5,043,775 A | 8/1991 | Lee | |
| 5,252,804 A | 10/1993 | Griffaton | |
| 5,504,762 A | 4/1996 | Hutchison | |
| 5,668,826 A | 9/1997 | Bezinge et al. | |
| 5,809,050 A | 9/1998 | Baldwin et al. | |
| 6,061,374 A | 5/2000 | Nightingale et al. | |

FOREIGN PATENT DOCUMENTS

| | | |
|---|---|---|
| DE | 2832847 | 2/1980 |
| DE | 2950124 | 2/1984 |
| DE | 19909595 | 9/2000 |
| EP | 939309 | 9/1999 |
| FR | 2682476 | 4/1993 |

(Continued)

OTHER PUBLICATIONS

Search Report of EP 03 02 9380.

*Primary Examiner*—Tu T. Nguyen
(74) *Attorney, Agent, or Firm*—Pearl Cohen Zedek Latzer, LLP

(57) ABSTRACT

An arrangement for monitoring the power delivered by a photon channeling element including an integrating chamber to receive an output end of the photon channeling element and an optical surface positioned to reflect a portion of the laser-light exiting the photon channeling element at substantially normal incidence to the beam centerline. The integrating chamber may be adapted to collect substantially all of the laser-light reflected from the optical surface. The arrangement may also include a sensor in optical contact with a portion of the integrating chamber that is out of the path of laser-light reflected from the optical surface.

6 Claims, 3 Drawing Sheets

FOREIGN PATENT DOCUMENTS

| | | |
|---|---|---|
| JP | 59090027 | 5/1984 |
| JP | 01030034 | 1/1989 |
| JP | 03091283 | 4/1991 |
| JP | 08036122 | 2/1996 |
| WO | WO 98/35411 | 8/1998 |

* cited by examiner

ARRANGEMENT FOR MONITORING THE POWER DELIVERY OF A PHOTON CHANNELING ELEMENT

PRIORITY

This application is a Continuation-In-Part of Prior U.S. patent application Ser. No. 09/602,442, filed on Jun. 23, 2000 abandoned, and entitled: POWER MONITORING ARRANGEMENT FOR BROKEN FIBER DETECTOR, which claims a priority date from U.S. Provisional Application No. 60/147,562, filed on Aug. 6, 1999, and entitled: POWER MONITORING ARRANGEMENT FOR BROKEN FIBER SENSOR.

FIELD OF THE INVENTION

The present invention relates in general to monitoring the power delivery of a photon channeling element delivering laser-light from a source thereof to an apparatus or a site at which the laser-light is to be used. The invention relates in particular to an arrangement for determining the power of laser-light exiting a photon channeling element at the delivery-end thereof.

BACKGROUND

Photon channeling elements, such as optical fibers, waveguides, articulated arms and others, are used extensively in medical laser systems for delivering light from a laser to a site to be treated or to an optical system for shaping or focusing the laser-light for purposes of the treatment. In many such systems the delivery-end of a photon channeling element is connected to a handpiece used by an operator of the system to direct the laser-light. The handpiece may incorporate an optical system for focusing, shaping or further directing laser-light exiting the photon channeling element.

One well-known principle which is used in prior-art arrangements for detecting energy leakage from or damage to the photon channeling element is to monitor the power of laser-light at the delivery-end of the photon channeling element. The monitored power is compared electronically either with power monitored at the entrance-end of the photon channeling element or with a predetermined reference level representative of power delivered by the photon channeling element in an undamaged condition.

One particular problem in measuring power at the delivery-end of a photon channeling element incorporated in a handpiece, of course, is finding sufficient space for a sampling arrangement to divert a portion of the light exiting the optical fiber for measurement purposes. By way of example, prior-art arrangements have included a beamsplitter to divert a portion of the delivered light to a sensor for monitoring. In another arrangement, what might be described as a scraping arrangement, an aperture stop in the path of the delivered light is used for selecting a portion of light to be measured. This latter arrangement is disclosed in U.S. Pat. No. 4,556,875.

Even where space is available in a handpiece for such arrangements, a problem in using such arrangements may result from variations in form or polarization of a beam of laser-light exiting the optical fiber. Such variations result from changes in the form and amount of bends in the optical delivery element which occur as the handpiece is used by the operator. Such variations in form and polarization of an exiting beam could result in significant variations in detected power, even without damage or breakage of the photon channeling element. This in turn, could result in false indication of damage or breakage. There is a need for an arrangement for monitoring power in a beam of light exiting a photon channeling element which is small enough to be accommodated in a handpiece or the like and which is insensitive to geometry and/or polarization variations in the exiting beam.

SUMMARY OF THE INVENTION

Some embodiments of the present invention relate to an arrangement for monitoring the power delivered by a photon channeling element. The arrangement may include an integrating chamber to receive an output end of the photon channeling element and an optical surface positioned to reflect a portion of the laser-light exiting the photon channeling element at substantially normal incidence to the beam centerline. The integrating chamber may be adapted to collect substantially all of the laser-light reflected from the optical surface. The arrangement may also include a sensor in optical contact with a portion of the integrating chamber that is out of the path of laser-light reflected from the optical surface.

According to one embodiment of the present invention, laser-light reflected from the optical surface may scatter and re-scatter within the integrating chamber, such that the chamber may be substantially evenly illuminated. The sensor may be configured to detect at least a portion of the ambient light illuminating the chamber that is not directly reflected from the optical surface. The detected light may be associated with the power of the laser-beam exiting the photon channeling element, as will be explained in more detail hereinbelow.

BRIEF DESCRIPTION OF THE DRAWINGS

The subject matter regarded as the invention, is particularly pointed out and distinctly claimed in the concluding portion of the specification. The invention, however, both as to organization and method of operation, together with objects, features and advantages thereof, may best be understood by reference to the following non limiting detailed description when read with the accompanied drawings in which:

Figure 1:
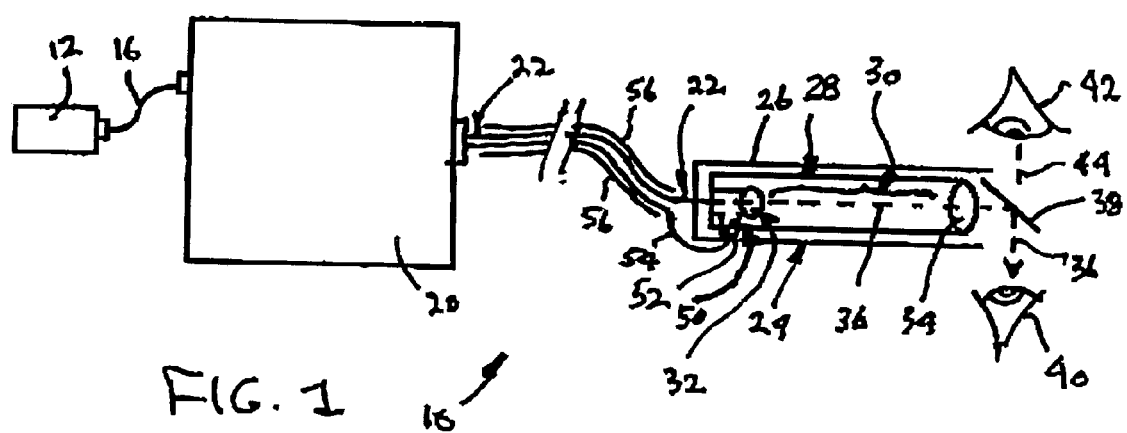
FIG. 1 schematically illustrates a diode-laser system for treating age-related macular degeneration, the system including a optical assembly attachable to a slit lamp microscope and an optical fiber for delivering laser-light from a diode-laser array to an optical system contained in the optical assembly, the optical assembly including one embodiment of a power monitoring arrangement in accordance with the present invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However it will be understood by those of ordinary skill in the art that the present invention may be practiced without these specific details. In other instances, well-known methods and procedures have not been described in detail so as not to obscure the present invention.

Throughout the specification and the claims, the term "ambient light" may be used to describe the light illuminating the integrating chamber as a result the scattering and re-scattering of the light reflected from the optical surface, with the exclusion of the main beam laser-light exiting the photon channeling element and the light directly reflected from the optical surface.

Some embodiments of the present invention relate to an arrangement for monitoring the power delivered by a photon channeling element. The arrangement may include an integrating chamber to receive an output end of the photon channeling element and an optical surface positioned to reflect a portion of the laser-light exiting the photon channeling element at substantially normal incidence to the beam centerline. The integrating chamber may be adapted to collect substantially all of the laser-light reflected from the optical surface. The arrangement may also include a sensor in optical contact with a portion of the integrating chamber that is out of the path of laser-light reflected from the optical surface.

According to one embodiment of the present invention, laser-light reflected from the optical surface may scatter and re-scatter within the integrating chamber, such that the chamber may be substantially evenly illuminated (with the exclusion of the main beam laser-light exiting the photon channeling element and the light directly reflected by the optical surface). Those of ordinary skill in the art may appreciate that the power of the ambient light within the integrating chamber may constant relative to the total amount of light collected by the integrating chamber. The sensor may be configured to detect at least a portion of the ambient light illuminating the chamber that is not directly reflected from the optical surface. The detected light may be associated with the power of the laser-beam exiting the photon channeling element, as will be explained in more detail hereinbelow.

As is well known, when using some optical channeling elements to deliver laser-light from an laser source, slight movements or bending of the photon channeling element may cause variations to the polarization, divergence angle, mode pattern or other characteristics of the laser-light exiting the photon channeling element. These variations may cause inaccuracies when attempting to monitor the power delivered by a photon channeling element. Some embodiments of the present invention, may be directed towards eliminating the effect of such variations upon the amount of light detected by the sensor, such that the amount of light detected by the sensor is substantially representative of the power that is actually delivered by the photon channeling element.

The positioning of the optical surface, such that the optical surface may reflect a portion of the laser-light exiting the photon channeling element at substantially normal angle of incidence to the beam centerline, may substantially reduce the sensitivity of the optical surface to variations related to the polarization state of the laser light. In other words, the positioning of the optical surface, such that the optical surface may reflect a portion of the laser-light exiting the photon channeling element at substantially normal angle of incidence, may render the amount of light that may be reflected by the optical surface less dependent upon variations related to the polarization state of the laser light. This may be contributable, at least in part, to the substantially limited effect of beam polarization upon the reflection of light from an optical surface, when the light is reflected from the optical surface at a substantially normal angle of incidence to the beam centerline.

The sensitivity of the light reflected by the optical surface to variations in the geometry of the laser-light may also be reduced, due to the scattering and re-scattering of the reflected light within the integrating chamber. The scattering and re-scattering of the reflected light within the integrating chamber may cause the light to be substantially evenly distributed within the chamber, such that the fraction of ambient light at each point within the integrating chamber is constant relative to the total amount of light collected by the integrating chamber. Thus, the ambient light within the integrating chamber may be substantially independent of such variations. The isolation of the sensor to light directly reflected from the optical surface, may enable the sensor to detect only the ambient light within the integrating chamber. Accordingly, a substantially beam geometry variations independent detection may be achieved, while maintaining association with the power of the laser-beam exiting the photon channeling element.

It should be noted that the combination of the substantially normal incidence reflections and the use of the integrating chamber the scatter and re-scatter the reflected light may substantially eliminate variations in detected light due to such variation in polarization, divergence angle, mode pattern or other characteristics of the laser-light exiting the photon channeling element.

According to some embodiments of the present invention the optical surface may be configured to reflect the laser-light, such that the incident angles of the reflected light are large enough to spread the reflected beam into the integrating chamber, without being large enough to cause significant difference in the light reflected as a function of polarization. According to yet further embodiments of the present invention, the optical surface may be configured to reflect the laser-light substantially symmetrically around the centerline of the laser-light exiting the photon channeling element.

The optical surface may be a curved surface of an optical element having at least one curved surface. The optical surface may be a spherical surface of an optical element having at least one spherical surface, such as a lens. The optical surface may be symmetrical positioned to reflect the laser-light exiting the photon channeling element substantially symmetrically around the centerline of the laser-light. Other optical surface and other optical elements may be used.

When using a multi mode photon channeling element, such as a multi mode optical fiber, some divergence in the laser-light exiting the photon channeling element may occur. In case such a multimode photon channeling element is used, a flat optical surface may be capable of sufficiently reflecting the laser-light exiting the photon channeling element into the integrating chamber. The divergence of the laser-light impinging upon the flat surfaces may enable the reflectance of light away from the laser-light centerline.

Subsequently, the light reflected away from such flat optical surfaces may be scattered and re-scattered by the integrating chamber, similarly to what was described above. Examples of such flat optical surface may include, but are not limited to a flat piece of glass, a flat surface or surfaces of a prism and other suitable flat surfaces of other optical elements.

As part of some embodiments of the present invention the optical surface may be part of any current or yet to be devised treatment accessories that may be coupled to and cooperatively operated with the integrating chamber. Such treatment accessories may include for example, a hanpiedce, an articulated arm, an output coupler, and other suitable treatment accessories including an optical surface.

According to some embodiments of the present invention, the integrating chamber may further include a diffusive medium, a diffusive coating, a diffusive design or any combination thereof. The diffusive medium, the diffusive coating and the diffusive design either individually or cooperatively may enhance the scattering and the re-scattering of the reflected light within the integrating chamber. The diffusive medium, the diffusive coating and the diffusive design either individually or cooperatively may also provide a specific scattering and re-scattering pattern. Such diffusive coating, medium and/or design either individually or cooperatively may reduce the likelihood of false or inaccurate detection by the sensor. False or inaccurate detection by the sensor that may occur, for example, due to inconsistent scattering of the reflected light, that may be contributable, for example, at least in part, to the defects in the integrating chamber surface.

The diffusive coating may include a diffusive agent, such as white-color coating the inner surface or surfaces of the integrating chamber. Other diffusive substances may be used. The diffusive medium may include a doughnut-like shaped translucent diffusive element having a substantially transparent central portion to allow the laser-light exiting the photon channeling element to pass through substantially unaffected. The diffusive medium may be in optical contact with the sensor. The outer surface of the diffusive medium may be evenly illuminated by the reflected light regardless of the geometry or the direction of the reflected light entering the diffusive medium. Other designs of the diffusive medium may be used to provide substantially even illumination to be detected by the sensor. Similarly the integrating chamber may be designed to provide substantially even illumination to be detected by the sensor. Other diffusive design may be used.

Some embodiments of the present invention are directed towards an apparatus and a method of monitoring power of laser-light delivered by a photon channeling element from a laser to an optical system. The photon channeling element may include an output end from which the laser-light may be delivered and the optical system may include a lens axially spaced apart from the optical fiber. The power monitoring method may include positioning a sensor facing the space between the optical fiber and the optical element such that the sensor may not directly receive laser-light reflected or scattered by the lens. Instead, the sensor may indirectly receive a portion of reflected or scattered laser-light via multiple reflection events. The received light may provide a signal representative of the power of laser-light delivered by the optical fiber.

In one example of the inventive method, the multiple reflection events may occur, inter alia, via reflection or scattering from an end face of the optical fiber, a wall of a housing in which the lens and the delivery-end of the optical fiber are located, and the lens itself. The sensor may be in optical communication with the space between the lens and the optical fiber via an aperture in the wall of the housing. The sensor may be arranged with respect to the aperture such that laser-light reflected or scattered from the lens may not reach the sensor directly. The lens and the optical fiber may be sufficiently closely spaced that the lens may collect all laser-light delivered by the optical fiber under any variations of beam-shape of the delivered laser-light resulting from changes in the path or form of the optical fiber to the optical system. This, together with preventing the sensor from receiving direct reflection or scatter from the lens, may minimize the effects of such variations in beam shape.

Turning now to the drawings, wherein like components are designated by like reference numerals, FIG. 1 schematically illustrates a diode-laser system 10 for treating age-related macular degeneration. System 10 includes a diode-laser array package 12 providing laser-light at having a wavelength of 689 nanometers (nm). This laser-light is the light used for treatment.

Laser-light from a diode-laser array package 12 is transmitted by an optical fiber 16 to a beam-conditioning and control unit 20. Control unit 20 includes means for attenuating the treatment laser-light, and means for monitoring power in the treatment laser-light. A diode-laser (not shown) located in control unit 20 provides laser-light at a wavelength of about 635 nm. This 635 nm laser-light is used for beam-aiming purposes. Control unit 20 includes means for combining aiming and treatment laser-light along a common optical path, and means for focusing the combined aiming and treatment light into an optical fiber 22. Control unit 20 also includes monitoring and control circuitry necessary for operating the system.

Figure 2:
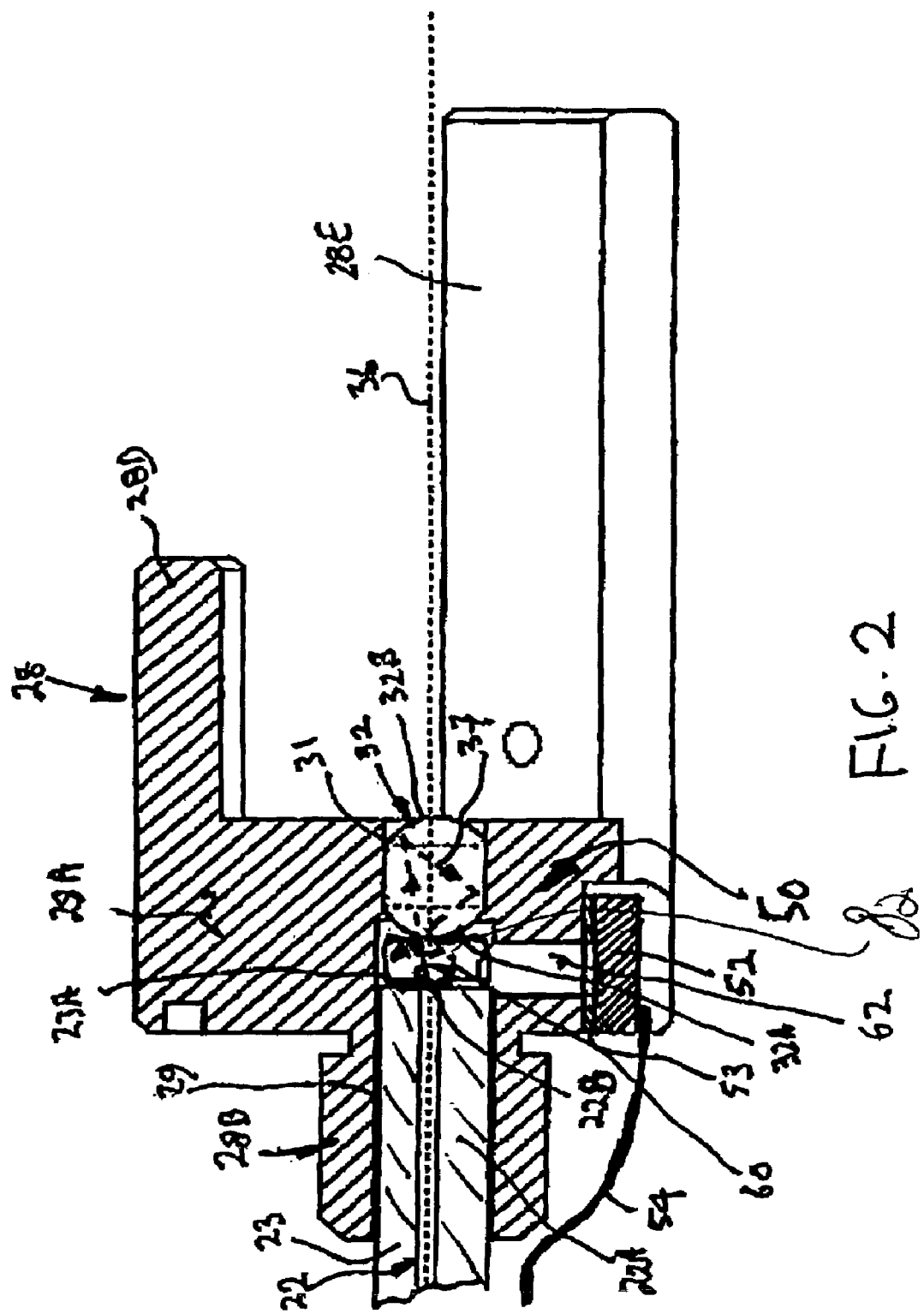
FIG. 2 is a side-elevation view, partly in cross-section, of an optical fiber connected to a lens-cell incorporated in the optical assembly of FIG. 1, schematically illustrating details of the power monitoring arrangement of FIG. 1.

Optical fiber 22 transports the aiming and treatment laser-light to an assembly 24 having an enclosure 26. Assembly 24 includes a lens-cell 28 located in enclosure 26. Lens-cell 28 includes an optical system 30 including one or more lenses or lens-elements. Only first and last lenses 32 and 34 respectively, are illustrated in FIG. 2. Lens 32 immediately follows optical fiber 22 in the direction of light transmitted thereby (illustrated schematically by dotted line 36). Light passing through lens 34 is directed by a 45 degree mirror 38 to an eye 40 being treated. Mirror 38 is selectively-reflective for treatment and laser-light wavelengths and transmissive for other visible light wavelengths. Aiming and treatment are observed by operator 42 through mirror 38 as indicated by dotted line 44.

A monitoring arrangement 50 in accordance with the present invention is located in assembly 24. The monitoring arrangement includes a sensor 52 situated generally between the exit-end (delivery-end) of optical fiber 22 and lens 32, but entirely out of the path of light exiting optical fiber 22. Sensor 52 is electrically connected by leads 54 (only one thereof shown for clarity) to control unit 20. Optical fiber 22 and leads 54 are gathered within an umbilical sheath indicated in FIG. 1 by lines 56.

Figure 3:
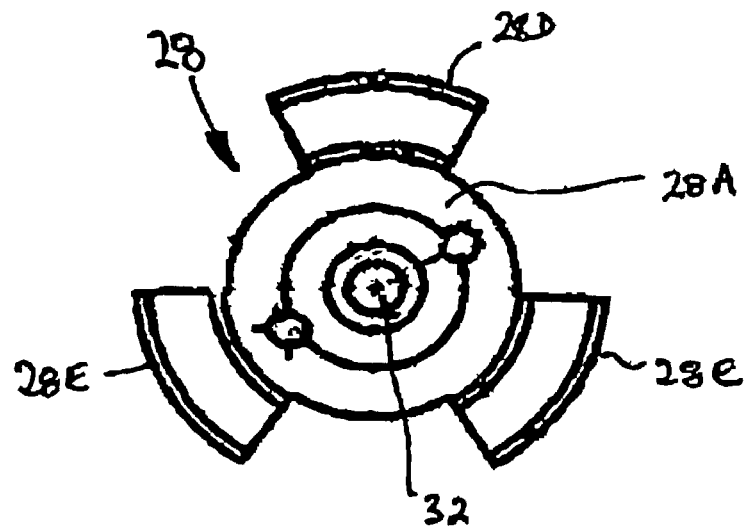
FIG. 3 is an end-elevation view schematically illustrating details of the lens-cell of FIG. 2.
Figure 4:
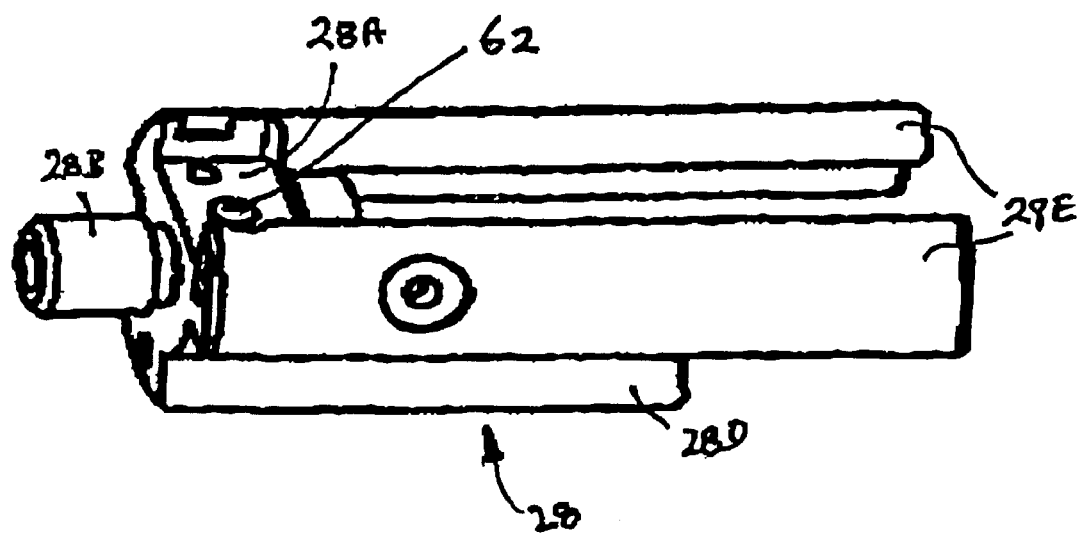
FIG. 4 is a three-dimensional view schematically illustrating further details of the lens-cell of FIG. 2.

Turning now to FIGS. 2, 3, and 4, with particular reference to FIG. 2, details of monitoring arrangement 50 are illustrated. Here, lens-cell 28 includes a body portion 28A. Extending from body portion 28A is a connector portion 28B. A bore 29 extends axially through connector portion 28B into body portion 28A. A further bore 31 extends from bore 29 through body portion 28A. Lens 32 is located in bore 31. Exit (distal) end 22A of optical fiber 22 is surrounded by a sheath 23. Exit face 22B of optical fiber 22 is flush with end face 23A of sheath 23.

Distal end 22A of optical fiber 22 and its surrounding sheath 23 are inserted into bore 29 such that end face 23A of the sheath is separated from surface 32A of lens 32 by a distance equal to about the diameter of bore 29. A space 60 between end face 23A of the fiber sheath is enclosed by the end fiber sheath and the walls of bore 29. As such, space 60 may be designated as a chamber or enclosure.

Another bore 62 extends transversely through body portion 28A of lens-cell 28 into enclosure 60. Sensor 52, preferably a silicon photodiode, is aligned with bore 62 and has optical access to enclosure 60. Sensor 52 is electrically isolated from lens-cell 28 by an insulator 53.

In one example of dimensions of the optical fiber/lens-cell arrangement of FIG. 2, lens 32, and sheath 23 have a diameter of about 3.0 millimeters (mm) and bores 29 and 31 are correspondingly sized. Optical fiber 22 has a diameter of about 200 micrometers ($\mu$m). The cone of divergence of laser-light exiting optical fiber 22 has a half-angle of about 8 degrees, i.e., a numerical aperture of about 0.14. The relatively close spacing of exit-face 22B of optical fiber 22 and lens 32 combined with a relatively large ratio of lens diameter to fiber diameter provides that lens 32 can collect all laser-light exiting optical fiber 22 under all anticipated variations of beam-shape resulting from changes in the path or bending of optical fiber 22 between assembly 24 and control unit 20. Although, here, arranged as an assembly attachable to a slit-lamp microscope, assembly 24 has general dimensions of a laser-delivery handpiece.

Some proportion of laser-light exiting optical fiber 22 and passing directly through lens 32 and a diffusive medium 82 is reflected or scattered from faces 32A and 32B of the lens or from sides of the lens, back into enclosure 60 to be received by the diffusive element 82, for example, as indicated schematically in FIG. 2 by dotted line 37. In enclosure 60 laser-light reflected or scattered from the lens is in turn intercepted by the diffusive medium 82 and scattered through out the enclosure 60. For purposes of this description and the appended claims these multiple scattering diffuse and specular reflections events are referred to collectively hereinafter simply as reflections. It has been found that a sufficient amount of this multiply-scattered light reaches sensor 52 via bore 62 that the sensor provides a signal of sufficient strength to be used for determining the power of laser-light exiting the fiber. Further, it has been found that the strength of the signal is insensitive to changes in the path or bending of optical fiber 22 between control unit 20 and assembly 24.

It is believed that the insensitivity of the monitored signal to changes in the path or bending of optical fiber results from the particular arrangement of the sensor with respect to exit face (end face) 22B of the optical fiber and lens 32. Those skilled in the art will recognize from the description provided herein that this arrangement prevents sensor 52 from receiving, directly, any light secularly reflected, diffusely reflected, or scattered from lens 32, as the sensor is positioned out of any direct line of sight with the lens. By directly, here, of course, is meant proceeding from the lens to the sensor without intermediate spectral reflection, diffuse reflection or scattering. Light proceeding indirectly from the lens to the sensor via above-discussed multiple reflections is believed not to be significantly affected by changes in the path or bending of optical fiber. This results from the above-discussed close spacing of the delivery-end of the fiber which ensures that all light emitted by the fiber is incident on lens 32 under all anticipated variations of beam-shape resulting from changes in the path or bending of optical fiber 22 between assembly 24 and control unit 20.

In exemplary system 10, power to be monitored may range from a lowest value of 1.5 mW for the aiming laser-light to a highest value of about 400 mW for the treatment laser-light. It is desirable to be able to monitor power of the aiming laser-light, as this provides a means of determining the integrity of optical fiber 22 before treatment is initiated. Monitoring power of treatment laser-light, of course, enables damage to optical fiber 22 to be determined in the course of treatment.

The amount of multiply reflected or scattered light can be increased by omitting an antireflection coating from one or more of faces 32A and 32B of lens 32. This can be effective in providing a greater signal for monitoring lower power levels. It has been found, for example, that omitting a coating from surface 32B is particularly effective in this regard. It has also been found that omitting an antireflection coating from surface 32B of lens 32 can be done without noticeably compromising optical performance of system 10. Those skilled in the art may devise other optical coating schemes, such as using "partially effective" reflection-reducing coatings which reduce reflection less than is usual in the art, or even by using coatings which slightly increase the reflection of a lens surface, without departing from the spirit and scope of the present invention.

Regarding electronically processing the signal from sensor 52 for the purpose of using monitored power to indicate optical fiber damage, this may be done by comparing monitored power with power monitored at the entrance (proximal) end of optical fiber 22, or by comparing the monitored power with predetermined reference levels. In one preferred arrangement of system 10, for example, damage is determined by comparing power monitored by sensor 52 with a electronic gain value which can be calibrated or adjusted to provide that a standard reference level is established which is independent of optical fiber and optical system variations which may be encountered in assembly or operation of the system.

Control unit 20 also includes an automatic range-switching arrangement for accommodating the relatively very large power difference between the aiming laser-light and the treatment laser-light. This enables essentially continuous monitoring of the integrity of optical fiber 22 before, during, and after treatment without operator intervention.

It should be noted here that in the description provided above, details of other elements of an optical system in handpiece 24 have been omitted as such details are not necessary for understanding principles of the present invention. In the example of system 10, the lens system is a zoom-lens system having a total of four elements, including movable elements. Lens-element 32 is a fixed element of that zoom-lens system. Other fixed and movable elements (not shown) are mounted in arms 28D and 28E extending from body portion 28A of lens-cell 28.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What we claim is:

1. An arrangement in a treatment device for monitoring the power delivered by a photon channeling element, comprising:

an integrating chamber to receive an output end of said photon channeling element and one or more optical surfaces positioned to reflect at least a portion of the laser-light exiting said photon channeling element, said one or more optical surfaces positioned at substantially normal incidence to a beam centerline of said laser-light, wherein said integrating chamber is configured to collect at least a portion of the laser-light reflected from said optical surfaces;

a sensor, said sensor being in optical contact with at least a portion of said integrating chamber, such that said sensor is exposed only to laser-light indirectly reflected from said optical surfaces, wherein said integrating chamber is adapted to scatter and re-scatter light reflected from said optical surfaces within the integrating chamber in a manner to provide a substantially evenly distributed ambient light illuminating said integrating chamber; and an output end from which the laser-light is delivered to a treatment surface.

2. The arrangement of claim 1, wherein said sensor is configured to detect at least a portion of said ambient light illuminating said integrating chamber.

3. The arrangement of claim 2, wherein the amount of ambient light detected by said sensor is associated with the amount of laser-light delivered by said photon channeling element.

4. The arrangement of claim 3, wherein said sensor is adapted to produce a signal indicative of the amount of laser-light delivered by said photon channeling element.

5. The arrangement of claim 4, wherein said sensor is adapted to produce a signal representative of the integrity or the lack of integrity of said photon channeling element.

6. An arrangement in a treatment device for monitoring the power delivered by a photon channeling element, comprising:

an integrating chamber to receive an output end of said photon channeling element and one or more optical surfaces positioned to reflect at least a portion of the laser-light exiting said photon channeling element, said one or more optical surfaces positioned at substantially normal incidence to a beam centerline of said laser-light, wherein said integrating chamber is configured to collect at least a portion of the laser-light reflected from said optical surfaces; and a sensor, said sensor being in optical contact with at least a portion of said integrating chamber, such that said sensor is exposed only to laser-light indirectly reflected from said optical surfaces, wherein said output end of said photon channeling element and said optical surfaces are positioned on either end of a first inner bore within said integrating chamber, said bore extending substantially around the beam centerline, and optically connected to a second inner bore substantially orthogonal to said first inner bore, wherein said sensor is positioned within said second inner bore, such that said sensor is exposed only to laser-light indirectly reflected from said optical surfaces; and an output end from which the laser-light is delivered to a treatment surface.

* * * * *